United States Patent [19]  
Moreschini et al.

[11] 3,968,149  
[45] July 6, 1976

[54] PROCESS FOR THE ESTERIFICATION IN VAPOR PHASE OF ALPHA, BETA-UNSATURATED MONOCARBOXYLIC ACIDS

[75] Inventors: Luciano Moreschini; Guido Petrini, both of Milan; Leonardo Dalloro, Bollate (Milan), all of Italy

[73] Assignee: Montedison S.p.A., Milan, Italy

[22] Filed: Mar. 6, 1975

[21] Appl. No.: 556,160

[30] Foreign Application Priority Data
Mar. 7, 1974 Italy .................................. 49121/74

[52] U.S. Cl. ............................ 260/486 R; 252/438; 252/458; 260/486 D

[51] Int. Cl.² ........................................ C07C 69/54
[58] Field of Search ................................ 260/486 R

[56] References Cited
UNITED STATES PATENTS

| 3,442,934 | 5/1969 | Pine | 260/486 R |
| 3,442,935 | 5/1969 | Pine | 260/486 R |

Primary Examiner—Paul J. Killos

[57] ABSTRACT

Alpha, beta-unsaturated monocarboxylic acids, in particular methacrylic acid, are esterified in the vapor phase in contact with a catalyst containing, in combination with oxygen, tungsten alone or in admixture with one or more of the elements lithium, sodium, potassium, rubidium and cesium.

9 Claims, No Drawings

PROCESS FOR THE ESTERIFICATION IN VAPOR PHASE OF ALPHA, BETA-UNSATURATED MONOCARBOXYLIC ACIDS

THE PRIOR ART

The catalytic vapor phase esterification of alpha, beta-unsaturated monocarboxylic acids, such as acrylic acid and methacrylic acid is known and has been described. For instance, U.S. Pat. No. 2,947,779 describes such a process in which the catalyst is silica gel. In a more recently described process, (Br. Pat. No. 1,179,356), the catalyst employed is based on titanium, silicium and antimony oxides, variously combined.

THE PRESENT INVENTION

An object of this invention is to provide an improved process for the catalytic esterification of alpha, beta-unsaturated monocarboxylic acids in the vapor phase.

This and other objects are achieved by the invention in accordance with which the vapor phase esterification of alpha, beta-unsaturated monocarboxylic acids, and more particularly of methacrylic acid, is carried out in the presence of a catalyst containing, in combination with oxygen, either tungsten alone or tungsten in admixture with one or more of the elements lithium, sodium, potassium, rubidium and cesium.

The present process is particularly useful in the vapor phase esterification of acrylic and methacrylic acids. However, it is also useful, with especially satisfactory results, in the vapor phase esterification of other alpha, beta-unsaturated monocarboxylic acids, in particular alpha-ethylacrylic acid and crotonic acid.

Any primary aliphatic alcohol containing from 1 to 8 carbon atoms, linear or branched, can be used in this process.

The catalyst used according to this invention is not adversely affected, in general, by the presence of impurities in the reactants or of polymerization inhibitors for the unsaturated acids.

Another advantage of this process is that the esterification reaction can be carried out in the presence of a high concentration of $H_2O$ in the vapor phase. Thus, for instance, it is particularly convenient to use diluted solutions of methacrylic acid coming directly from the oxidation of methacrolein or from the oxidative dehydrogenation of isobutyrric acid, without burdensome concentrations and intermediate purifications. Gaseous reaction mixtures coming directly from the aforesaid oxidation processes can also be used.

The alcohol in the reaction mixture must be in excess of the stoichiometric quantity; the alcohol/acid molar ratio is thus greater than 1 and may be as high as 6.

The amount of unsaturated acid in the gaseous mixture of the reactants fed to the reactor is preferably between 1 and 15% by volume. Optionally, inert gaseous diluents such as nitrogen, $CO_2$, etc., can be present.

The elements are present in the catalytic compositions in quantities such that the atomic ratios between them correspond to the empirical formula:

wherein
Me is one or more of the elements Li, Na, K Rb and Cs;
$x$ is zero or a positive from 0,1 to 10;
$z$ is a number which satisfies the valencies of the elements in the oxidation stages in which they exist in the catalyst.

The catalytic compositions used in the process of this invention can be used without a carrier and, as such, exhibit excellent catalytic activity. However, a carrier may be used, if desired, and may be any material suitable for the purpose such as, for instance, silica, alumina, carborundum, silica-alumina, silicates, borates, or carbonates, provided they are stable under the reaction conditions. If a carrier is used, the quantity of active catalytic composition with respect to the weight of the carrier, or support, can vary within wide limits, depending on the characteristics of the carrier and on the method by which the supported catalytic composition is prepared.

The process of the invention can be carried out using the catalyst in the form of either a fixed or fluidized bed. In the latter embodiment, the nature, or character, of the carrier and the method of obtaining a microspheroidal catalyst having a suitable granulometric distribution are of particular importance.

A microspheroidal catalyst can be obtained by different methods, for instance by spray-drying a solution or suspension of the carrier and of the components of the catalytically active composition, or by soaking a preformed microspheroidal carrier in a solution of the components of the catalytically active composition.

As starting compounds of Li, Na, K Rb and/or Cs for the preparation of the catalytic compositions of the invention there may be used, for example, the following alkaline metal compounds; nitrates, oxides, hydroxides, carbonates, bicarbonates, nitrites, silicates, and the salts of oxy-acids or of organic mono- or poly-carboxylic acids such as formates, oxalates, citrates, tartrates, etc.

In the presently preferred embodiment of this invention, the starting tungsten compound is silico-tungstic acid. However, salts of tungstic acid can also be used.

All methods of preparing the catalytic compositions include a final activation step which consists in heating the compositions in the presence of air or of a mixture of air and steam at a temperature of from 350°C to 850°C, preferably from 400°C to 700°C.

The catalytic compositions can be prepared by methods known in general; those which we have used to prepare the catalytic compositions include the following:

1. A catalyst consisting of about 20% of $WO_3$ and 80% of silica was prepared by dissolving 56 gm. of ammonium-metatungstate $[(NH_4)_6H_2W_{12}O_{40}.xH_2O]$ containing about 90% of $WO_3$ in water to obtain 230 cc of solution. 200 gms. commercial microspheroidal silica were impregnated with the solution. The product thus obtained was dried in an oven for 12 hours at 130°C and then activated in a muffle-furnace for 2 hours at 540°C.

2. 200 gms. of commercial microspheroidal silica were soaked in a solution prepared by dissolving 52 gms. of silico-tungstic acid $(SiO_2.12WO_3.26H_2O)$ in 200 ccs. of water and adding 6.3 gm. of potassium nitrate. The product obtained was dried in an oven for 12 hours at 130°C and then activated in a muffle-furnace for 2 hours at 400°C.

3. To 100 gm. of ammonium paratungstate $[5(NH_4)2O_{12}WO_3. 5H_2O]$ were added 3.2 gm. of potassium nitrate and 150 ccs. of water. The mass was slowly brought to dryness and then further dried at 130°C for 12 hours. The residue was activated in air for 2 hours at 400°C.

Using the catalysts described, selectivities in ester very close to 100 percent are obtained, with high conversions of the alpha, beta-unsaturated monocarboxylic acid.

In practicing the present invention, the reactants may be fed onto the catalyst completely pre-mixed, partially pre-mixed or separately. Feeding of the separate or partially pre-mixed reactants may be more convenient when a fluid bed reactor is employed.

When the reaction is conducted using a fixed catalytic bed, the bed can be realized according to methods known in general, for example by placing the catalyst inside the pipes of a pipe-bundle reactor and removing the reaction heat by suitable heat-exchange fluids circulating on the outside of the pipes and, more commonly, by means of mixtures of molten salts. It is also possible to operate in a reactor consisting of several adiabatic reaction stages alternating with zones for cooling the reaction mixture.

The esterfication reaction is conducted at a temperature comprised between 150°C and 350°C, preferably at from 180°C to 280°C.

The contact time, expressed in seconds as a ratio between the volume of the catalytic bed and the volumes per second of gaseous reactant mixture fed in, measured under the average conditions of temperature and pressure existing in the catalytic bed, may vary depending on the specific nature of the catalyst, the kind of catalytic bed used, whether fixed or fluidized, and on the size of the catalyst. In general, the contact time is from 3 to 50 seconds. A contact time of from 5 to 25 seconds is presently preferred because it corresponds to the most common practical working conditions.

The total pressure under which the reaction is conducted is not particularly critical and can vary within wide limits. However, it is partly suggested by economical considerations and, therefore, it is presently preferred to operate at atmospheric pressure or at pressures only slightly higher than atmospheric.

The alpha, beta-unsaturated acid ester obtained can be separated from the other reaction products by conventional distillation and extraction techniques.

The following examples are given to illustrate the invention in more detail and are not intended to be limiting.

EXAMPLE 1

The catalyst was prepared by method (1) as described hereinabove; consisted for 80% of microspheroidal $SiO_2$ as carrier and for the remainder of an active part in which the atomic ratio between the elements composing it, W and O, was 1:3.

The esterification reaction in vapor phase was carried out in a reactor filled with the above indicated catalyst in the form of a fluid bed. The fed mixture consisted of methacrylic acid, methanol and water in molar ratios of 1:4:14.

The reaction temperature was 210°C while the contact time was 18 seconds.

On the basis of the gas chromatographic analysis of the reaction gases, there was calculated a 79.2% conversion of the fed methacrylic acid and a selectivity of 93.6% in methylmetacrylate. By the term selectivity is meant the ratio:

$$\frac{\text{moles of obtained methylmethacrylate}}{\text{moles of reacted methacrylic acid}} \times 100$$

EXAMPLE 2

The catalyst used in this test was the same as that of Example 1, and also in this case the esterification reaction in vapor phase was conducted in a catalytic fluid bed reactor.

The fed mixture consisted of methacrylic acid, methanol and water in molar ratios of 1:4:14.

The reaction temperature was 180°C and the contact time was 25 seconds. On the basis of the gas-chromatographic analysis of the reaction gases, a yield in methylmethacrylate was calculated of 60.2 percent, meaning by the expression "yield" the ratio:

$$\frac{\text{moles of obtained methylmethacrylate}}{\text{moles of fed in methacrylic acid}} \times 100$$

EXAMPLE 3

The catalyst was prepared by method (2) described hereinabove.

The esterification reaction in vapor phase was carried out in a reactor filled with the above indicated catalyst having the form of a fluidized bed. The fed mixture consisted of methacrylic acid, methanol and water in molar ratios of 1:5:14.

The reaction temperature was 260°C and the contact time was 7 seconds. On the basis of the gas-chromatographic analysis of the reaction gases, the conversion of fed methacrylic acid was calculated as 71.1 percent, while the selectivity in methymethacrylate was found to be 95.8 percent. A selectivity in acetone of 3.3 percent and a selectivity in propylene of 0.9 percent was found.

EXAMPLE 4

The catalyst used was the same as that of Example 3 and also in this case the esterification reaction was conducted in a catalytic fluidized bed reactor.

The fed mixture consisted of methacrylic acid, methanol and water in molar ratios equal to 1:4:14.

The reaction temperature was 340°C and the contact time was 6 seconds.

On the basis of the gas-chromatographic analysis of the reaction gases, it was calculated that there was a yield in methylmethacrylate of 63%.

EXAMPLE 5

The catalyst was prepared according to the above described method (3). The esterification reaction in vapor phase was carried out in a reactor filled with the above mentioned catalyst in the form of a fixed bed.

The fed mixture consisted of methacrylic acid, methanol and water, in molar ratios 1:6:14.

The reaction temperature was 260°C, while the contact time was 20 seconds.

On the basis of the gas-chromatographic analysis of the reaction gases, there was calculated a conversion of the fed methacrylic acid of 80 percent and a selectivity in methylmethacrylate of 88 percent.

We claim:

1. A process for producing esters of alpha, beta-unsaturated monocarboxylic acids using as one reactant the raw acid having a high water content, which comprises reacting the acid with primary aliphatic alcohols containing from 1 to 8 carbon atoms, in the vapor phase, at a temperature of from 150°C to 350°C, and in the presence of a catalytic composition containing oxygen and tungsten as the essential catalyst-forming elements and, optionally, at least one of the elements lithium, sodium, potassium, rubidium and cesium, said elements being present in the catalyst in quantities such that the atomic ratios correspond to the empirical formula:

$$W_{12}O_zMe_x$$

wherein
Me is one or more of the elements Li, Na, K, Rb and Cs;
$x$ is zero or a positive from 0,1 to 10; and
$z$ is a number which satisfies the mean valencies of the elements in the oxidation state in which they exist in the catalytic combination.

2. The process of claim 1, in which the esterification reaction is carried out at a temperature of from 180°C and 280°C.

3. The process of claim 1, in which the catalytic composition is supported on a carrier consisting of a material which is stable under the reaction conditions.

4. The process of claim 3, in which the carrier is silica, alumina, carborundum, silica-alumina, a silicate, a borate or a carbonate.

5. The process of claim 1, in which the gaseous esterification reaction mixture contains from 1 to 15% by volume of the alpha, beta-unsaturated monocarboxylic acid.

6. The process of claim 1, in which the alpha, beta-unsaturated acid is methacrylic acid.

7. The process of claim 1, in which the alpha, beta-unsaturated acid is acrylic acid.

8. The process of claim 5, in which the alpha, beta-unsaturated acid is methacrylic acid.

9. The process of claim 5, in which the alpha, beta-unsaturated acid is acrylic acid.

* * * * *